US012064172B2

(12) United States Patent
Hancock et al.

(10) Patent No.: US 12,064,172 B2
(45) Date of Patent: Aug. 20, 2024

(54) ELECTROSURGICAL APPARATUS FOR DELIVERING RF AND/OR MICROWAVE ENERGY INTO BIOLOGICAL TISSUE

(71) Applicant: CREO MEDICAL LIMITED, Chepstow (GB)

(72) Inventors: Christopher Paul Hancock, North East Somerset (GB); Rohan Monico, Chepstow (GB); Steve Morris, Chepstow (GB); Tom Craven, Chepstow (GB); Stefanie Pohlmann, Chepstow (GB)

(73) Assignee: CREO MEDICAL LIMITED, Chepstow Monmouthshire (GB)

( * ) Notice: Subject to any disclaimer, the term of this patent is extended or adjusted under 35 U.S.C. 154(b) by 159 days.

(21) Appl. No.: 16/624,742

(22) PCT Filed: Aug. 15, 2018

(86) PCT No.: PCT/EP2018/072155
§ 371 (c)(1),
(2) Date: Dec. 19, 2019

(87) PCT Pub. No.: WO2019/134710
PCT Pub. Date: Feb. 21, 2019

(65) Prior Publication Data
US 2020/0268445 A1    Aug. 27, 2020

(30) Foreign Application Priority Data

Aug. 17, 2017    (GB) ........................................ 1713177

(51) Int. Cl.
*A61B 18/18*    (2006.01)
*A61B 18/00*    (2006.01)

(52) U.S. Cl.
CPC ..................... *A61B 18/1815* (2013.01); *A61B 2018/00601* (2013.01); *A61B 2018/00982* (2013.01);
(Continued)

(58) Field of Classification Search
CPC ........ A61B 18/1815; A61B 2018/1876; A61B 2018/1861; A61B 17/3478
See application file for complete search history.

(56) References Cited

U.S. PATENT DOCUMENTS

| 6,210,396 B1 * | 4/2001 | MacDonald | A61L 31/18 604/103.1 |
| 2003/0088242 A1 * | 5/2003 | Prakash | A61B 18/18 606/33 |

(Continued)

FOREIGN PATENT DOCUMENTS

| EP | 2286754 A1 | 2/2011 |
| EP | 2377481 A1 | 10/2011 |

(Continued)

OTHER PUBLICATIONS

International Search Report and Written Opinion, issued by the International Searching Authority in corresponding International Application No. PCT/EP2018/072155, mailed Nov. 6, 2018.

(Continued)

*Primary Examiner* — Khadijeh A Vahdat
*Assistant Examiner* — Marina Delaney Templeton
(74) *Attorney, Agent, or Firm* — ArentFox Schiff LLP (57) ABSTRACT

An electrosurgical instrument for delivering electromagnetic energy to biological tissue, the instrument comprising an active tip having an electrically conductive protective hull mounted on an underside thereof. The hull has a smoothly contoured convex undersurface, and is formed as a shaped piece of electrically conductive bio-compatible material having a low coefficient of friction with biological tissue (Continued)

(e.g. stainless steel) which has the dual function of (i) physically protecting tissue that lies underneath the active tip, and (ii) providing an electrical connection between a coaxial feed line and the active tip.

14 Claims, 3 Drawing Sheets

(52) U.S. Cl.
CPC ............... *A61B 2018/1838* (2013.01); *A61B 2018/1861* (2013.01); *A61B 2018/1876* (2013.01)

(56) References Cited

U.S. PATENT DOCUMENTS

| | | | | |
|---|---|---|---|---|
| 2003/0125732 | A1* | 7/2003 | Goble | A61B 18/1402 606/48 |
| 2010/0228244 | A1* | 9/2010 | Hancock | A61B 18/1815 606/33 |
| 2013/0289557 | A1* | 10/2013 | Hancock | H01Q 13/08 606/33 |
| 2015/0196353 | A1* | 7/2015 | Hancock | A61B 18/042 606/46 |
| 2016/0175025 | A1* | 6/2016 | Strobl | A61B 18/1445 427/2.28 |

FOREIGN PATENT DOCUMENTS

| | | |
|---|---|---|
| GB | 2503673 A | 1/2014 |
| GB | 2523246 A | 8/2015 |

OTHER PUBLICATIONS

Search Report under Section 17(5), issued in corresponding British Patent Application No. GB1713177.2, dated Feb. 8, 2018.

* cited by examiner

SECTION A-A

ELECTROSURGICAL APPARATUS FOR DELIVERING RF AND/OR MICROWAVE ENERGY INTO BIOLOGICAL TISSUE

CROSS-REFERENCE TO RELATED APPLICATIONS

This application is a is a National Stage entry of International Application No PCT/EP2018/072155, filed on Aug. 15, 2018, which claims priority to British Patent Application No. 1713177.2, filed on Aug. 17, 2018. The disclosures of the priority applications are hereby incorporated in their entirety by reference.

FIELD OF THE INVENTION

The invention relates to an electrosurgical apparatus and device for delivering radiofrequency and/or microwave frequency energy into biological tissue. In particular, the invention relates to an electrosurgical instrument capable of delivering radiofrequency (RF) energy for cutting tissue and/or microwave frequency energy for haemostasis (i.e. promoting blood coagulation). The invention may be particularly suitable in gastrointestinal (GI) procedures associated with the lower and upper GI tract, e.g. to remove polyps on the bowel, i.e. for endoscopic mucosal resection, or endoscopic submucosal dissection. The invention may also lend itself to other procedure, e.g. in general surgery or laparoscopic surgery. The invention may find use in ear, nose and throat procedures and liver resection. The device may also be used to address procedures associated with the pancreas, e.g. to resect or remove tumours or abnormalities in close proximity to the portal vein or the pancreatic duct.

BACKGROUND TO THE INVENTION

Surgical resection is a means of removing sections of organs from within the human or animal body. Such organs may be highly vascular. When tissue is cut (divided or transected) small blood vessels called arterioles are damaged or ruptured. Initial bleeding is followed by a coagulation cascade where the blood is turned into a clot in an attempt to plug the bleeding point. During an operation, it is desirable for a patient to lose as little blood as possible, so various devices have been developed in an attempt to provide blood free cutting. For endoscopic procedures, bleeds are also undesirable, and need to be dealt with in an expedient manner, since the blood flow may obscure the operator's vision, which may prolong surgery and potentially lead to the procedure needing to be terminated and another method used instead, e.g. open surgery.

Electrosurgical generators are prevalent in hospital operating theatres, often for use in open and laparoscopic procedures, and increasingly for use with surgical scoping devices, e.g. an endoscope or the like. In endoscopic procedures the electrosurgical accessory is typically inserted through a lumen inside an endoscope. Considered against the equivalent access channel for laparoscopic surgery, such a lumen is comparatively narrow in bore and greater in length.

Instead of a sharp blade, it is known to use radiofrequency (RF) energy to cut biological tissue. The method of cutting using RF energy operates using the principle that as an electric current passes through a tissue matrix (aided by the ionic contents of the cells and the intercellular electrolytes), the impedance to the flow of electrons across the tissue generates heat. In practice, an instrument is arranged to apply an RF voltage across the tissue matrix that is sufficient to generate heat within the cells to vaporise the water content of the tissue. However, as a result of this increasing desiccation, particularly adjacent to the RF emitting region of the instrument (which has the highest current density of the current path through tissue), direct physical contact between the tissue and instrument can be lost. The applied voltage then manifests itself as a voltage drop across this small void, which causes ionisation in the void that leads to a plasma. Plasma has a very high volume resistivity compared with tissue. The energy supplied to the instrument maintains the plasma, i.e. completes the electrical circuit between the instrument and the tissue. Volatile material entering the plasma can be vaporised and the perception is therefore of a tissue dissecting plasma.

GB 2 523 246 describes an electrosurgical instrument for applying to biological tissue RF electromagnetic energy and/or microwave frequency EM energy. The instrument comprises a shaft insertable through an instrument channel of a surgical scoping device. At a distal end of the shaft there is an instrument tip comprising a planar transmission line formed from a sheet of a first dielectric material having first and second conductive layers on opposite surfaces thereof. The planar transmission line is connected to a coaxial cable conveyed by the shaft. The coaxial cable is arranged to deliver either microwave or RF energy to the planar transmission line. The coaxial cable comprises an inner conductor, an outer conductor coaxial with the inner conductor, and a second dielectric material separating the outer and inner conductors, the inner and outer conductors extending beyond the second dielectric at a connection interface to overlap opposite surfaces of the transmission line and electrically contact the first conductive layer and second conductive layer respectively. The instrument further comprises a protective hull with a smoothly contoured convex undersurface facing away from the planar transmission line. The undersurface comprises a longitudinally extending recessed channel formed therein. A retractable needle is mounted within the instrument, and operable to extend through the recessed channel to protrude from a distal end of the instrument. The needle can be used to inject fluid into a treatment zone before the RF or microwave energy is applied.

SUMMARY OF THE INVENTION

At its most general, the present invention provides a development to the concept discussed in GB 2 523 246. The development may include forming the protective hull as a shaped piece of electrically conductive bio-compatible material having a low coefficient of friction with biological tissue (e.g. stainless steel) which has the dual function of (i) physically protecting tissue that lies underneath the active tip, and (ii) providing an electrical connection between a coaxial feed line and the active tip.

The protective hull may be particularly useful in procedures performed in the gastrointestinal tract, where bowel perforation is a concern, or in the pancreas, where damage to the portal vein or the pancreatic duct may occur when a tumour or other abnormality is being resected, dissected or removed.

The protective hull may be applied to planar instrument tips adapted for different functions. For example, aspects of the invention contemplated herein include: an instrument adapted to deliver radiofrequency (RF) energy for cutting biological tissue; an instrument adapted to deliver both RF and microwave frequency energy separately or simultaneously; and an instrument adapted to deliver RF and/or microwave energy and having a retractable needle for delivering or removing fluid (liquid or gas) to or from the treatment site. For example, the needle may be used to introduce a gas, e.g. argon, to produce thermal or non-thermal plasma for surface coagulation (thermal) or sterilisation (non-thermal). The RF and/or microwave field may be used to strike and sustain or create this plasma. The protective hull may include a passageway, e.g. recessed channel, through which the retractable needle travels or through which fluid can be delivered without the use of a needle, e.g. for clinical or cleaning purposes.

According to the invention, there is provided an electrosurgical instrument for delivering electromagnetic energy to biological tissue, the instrument comprising: a distal end assembly comprising: an active tip comprising a planar body made of a first dielectric material separating a first conductive element on a first surface thereof from a second conductive element on a second surface thereof, the second surface facing in the opposite direction to the first surface; an electrically conductive protective hull mounted on an underside of the active tip, the protective hull having a smoothly contoured convex undersurface facing away from the planar body; and a coaxial feed cable comprising an inner conductor, an outer conductor coaxial with the inner conductor and a second dielectric material separating the inner and outer conductors, the coaxial feed cable being for conveying RF EM energy or microwave EM energy, wherein the inner conductor is electrically connected to the first conductive element and the outer conductor is electrically connected to the second conductive element via the protective hull to enable the instrument tip to receive the RF and/or the microwave signal, and wherein the first and second conductive elements are arranged to emit the RF EM energy or the microwave EM energy from the coaxial cable at a distal side portion of the planar body. With this arrangement, the protective hull itself provide a conductive path between the coaxial cable and the active tip, so that no additional connecting components are required.

The first and second conductive elements may be arranged to act as either or both of (i) active and return electrodes to emit RF EM energy, or (ii) an antenna structure for emitting and microwave EM energy from the distal side portion of the active tip.

The protective hull may be formed from a conductive material having a low coefficient of friction with biological tissue, and which is biocompatible. Stainless steel may be preferred.

The protective hull may be soldered to the second conductive element to provide the requisite electrical connection. The soldering may be performed after the protective hull and active tip are positioned together. The soldering may be induction soldering. A solder preform may be mounted between the protective hull and active tip to provide the material for the soldered joint. The protective hull may comprise an upper surface for abutting the second surface of the planar body. The upper surface may comprise a recess for retaining the solder preform. The recess may be rectangular. The recess may have side edges that are set back from side edges of the planar body. This can ensure that solder does not flow or leak to the sides of the active tip, where it could interfere with delivery of the RF EM energy or microwave EM energy.

The protective hull may have a U-shaped recess for receiving a portion of the outer conductor. For example, the outer conductor may be exposed along a length of the coaxial cable where it engages the protective hull. The coaxial cable may be retained in the U-shaped recess by an interference fit. In one example, the coaxial cable may be deformed, e.g. by a crimp or the like to cause it to abut and engage the U-shaped recess. The coaxial cable may be squashed so that its cross-section belong oval, whereby it engages side walls of the U-shaped recess.

The undersurface of the protective hull may smoothly taper at its perimeter to meet the underside of the planar body. The thickness of the protective hull may also decrease towards the distal end of the instrument tip. Thus, the outer portion of the protective hull may have a convex profile. The undersurface may have a longitudinally extending recessed channel formed therein. The tapering edge profile and recessed channel may cause the undersurface of the protective hull to comprise a pair of ridges. The tapered conformal flowing form of the hull may reduce the risk of the instrument digging into collateral tissue aiding its ability to glide. For example, this shape may reduce the risk of the instrument digging into the bowel wall and causing a bowel perforation or may protect the portal vein or pancreatic duct from being damaged. The particular dimensions of the hull (e.g. length, width, thickness, etc.) may be adapted to suit the intended use and intended area of the body to be operated on.

The distal end assembly may comprise a flexible shaft connected to a proximal end of the protective hull, the shaft defining a lumen for conveying the coaxial cable.

The flexible shaft may comprise a proximal cannula tube having braids formed therein to assist in the transfer of torque from its proximal end to the distal end assembly, and a distal unbraided tubular portion bonded to a distal end of the cannula tube. The braids may extend in a longitudinal direction. The braids may be made from metal. Providing the unbraided tubular portion can prevent the braids from interfering with the transfer of energy from the coaxial cable to the active tip.

The flexible shaft may comprise a support tube mounted at a junction between the proximal cannula tube and the unbraided tubular portion. The support tube may provide mechanical strength to the junction. The support tube may be a polymer sleeve to which the proximal cannula tube and the unbraided tubular portion are bonded. Additionally or alternatively, the junction between the proximal cannula tube and the unbraided tubular portion may be wrapped in a heat shrink sleeve.

The first and second conductive elements may be arranged to provide a local return path for RF energy, i.e. a low impedance route for RF energy to be transported between the first and second conductive elements. Meanwhile, for a microwave signal, the instrument tip may be modelled as a parallel plate transmission line with the planar body representing dielectric material separating two conductive plates.

The first and second conductive elements may each comprise a layer of metallisation being formed on opposite surfaces of the first dielectric material. The first and second conductive elements may be arranged to set up a local electric field at a contact region in which the instrument tip makes contact with the biological tissue. The local electric field can be extremely high, which may cause a microplasma (i.e. a hot thermal plasma) to be formed at the distal side portion of the planar body, e.g. where contact is made with the biological tissue. The microplasma may be desirable in terms of achieving efficient cutting. The first and second conductive elements may include portions, e.g. plated regions at and adjacent the distal side portion, made from conductive material having a high melting point, e.g. 1500° C. or more, such as titanium, tungsten or the like. Using such materials may prevent the high temperatures of the microplasma from eroding the first and second conductive elements. The first and second conductive elements may also include connecting portions made from conductive materials having lower melting points (e.g. silver, gold and the like) deposited or plated on the higher melting point conductors. The connecting portions may facilitate connection of the inner and outer conductors of the coaxial cable, e.g. by soldering or the like. In one embodiment, a titanium tungsten (TiW) seed layer may be used with a layer of silver (Ag) or gold (Au) deposited on the top. For example, the seed layer may have a thickness of 30 nm, and each layer of metallisation may have a thickness of 0.03 mm. Preferably, each layer of metallisation is deposited on the seed layer in two steps. In a first step, a 760 nm layer of silver or gold may be sputtered onto the seed layer. In a second step, a 29 μm thick layer of silver or gold may be deposited by electrolysis. The lower melting point material may be deposited onto the higher melting point material only in the region where the inner conductor and protective hull are to be attached, i.e. at the proximal end of the active tip only, and not along the sides thereof, where the microplasma will be generated.

In one embodiment, the first dielectric material separating the conductive elements may provide the preferential return path between the inner conductor (active) and the outer conductor (return). RF tissue cutting may be produced at the distal side portion of the instrument tip if the first dielectric material has a high dielectric constant (e.g. greater than that of air) and the thickness of the first dielectric material at the distal side portion, i.e. the separation of the first and second conductive elements at the distal side portion edge, is small, i.e. less than 1 mm. This arrangement may provide the necessary preferential return path for the current to flow.

The layers of metallisation may be set back (e.g. by 0.2 mm) from the side edges of the first dielectric material in a proximal region of the planar body, to reduce the field strength at this region. The proximal region may comprise the region of the planar body proximal to the distal end.

In some embodiments, the first dielectric material forming the planar body may be a biocompatible material such as ceramic, preferably alumina. For example, the first dielectric material may be at least 99% pure alumina having a polished surface for robust adhesion to the metallisation layers which may form the first conductive element and the second conductive element.

The distal end assembly may include a fluid feed conduit for conveying fluid for delivery out of the instrument. The undersurface of the protective hull may have a longitudinally extending recessed channel formed therein. The fluid feed conduit may be mounted within the longitudinally extending recessed channel. The coaxial feed cable may form part of a multi-lumen conduit assembly for delivering RF and/or microwave frequency energy and fluid (liquid or gas) to the instrument. The fluid may be conveyed through a corresponding passageway formed within the multi-lumen conduit assembly. The fluid feed conduit may also be used to deliver other material to the treatment site, e.g. a gas or a solid (e.g. powder). In one embodiment, injection of fluid (saline or the like) is used to plump up the biological tissue at the treatment site. This may be particularly useful where the instrument is used to treat the wall of the bowel or the wall of the oesophagus or for protecting the portal vein or the pancreatic duct when a tumour or other abnormality located in close proximity, in order to protect these structures and create a cushion of fluid. Plumping up the tissue in this manner may help to reduce the risk of bowel perforation, damage to the wall of the oesophagus or leakage of fluid from the pancreatic duct or damage to the portal vein, etc. This arrangement may enable the instrument to treat other conditions where the abnormality (tumour, growth, lump, etc.) is close to a sensitive biological structure.

The fluid feed conduit may comprise a needle guide tube having a retractable needle slidably mounted therein. The needle may be slidably movable with respect to the protective hull through one or more control wires, which may be actuated via a suitable slide actuator at a proximal end of the instrument. Preferably, the needle is slidable back and forth with respect to a fluid supply passageway which conveys the fluid to the needle for delivery. The fluid supply passageway may be an integral part of the sleeve, or may be a tube statically mounted in the sleeve. The ability to move the needle back and forth while conveying fluid to the needle through a conduit which does not move relatively to the sleeve enables a retractable needle to be provided within a smaller diameter sleeve than a device in which a fluid delivery tube must slide along the length of the sleeve.

The term "surgical scoping device" may be used herein to mean any surgical device provided with an insertion tube that is a rigid or flexible (e.g. steerable) conduit that is introduced into a patient's body during an invasive procedure. The insertion tube may include the instrument channel and an optical channel (e.g. for transmitting light to illuminate and/or capture images of a treatment site at the distal end of the insertion tube. The instrument channel may have a diameter suitable for receiving invasive surgical tools. The diameter of the instrument channel may be 5 mm or less.

Herein, the term "inner" means radially closer to the centre (e.g. axis) of the instrument channel and/or coaxial cable. The term "outer" means radially further from the centre (axis) of the instrument channel and/or coaxial cable.

The term "conductive" is used herein to mean electrically conductive, unless the context dictates otherwise.

Herein, the terms "proximal" and "distal" refer to the ends of the elongate probe. In use the proximal end is closer to a generator for providing the RF and/or microwave energy, whereas the distal end is further from the generator.

In this specification "microwave" may be used broadly to indicate a frequency range of 400 MHz to 100 GHz, but preferably the range 1 GHz to 60 GHz. Specific frequencies that have been considered are: 915 MHz, 2.45 GHz, 3.3 GHz, 5.8 GHz, 10 GHz, 14.5 GHz and 24 GHz. In contrast, this specification uses "radiofrequency" or "RF" to indicate a frequency range that is at least three orders of magnitude lower, e.g. up to 300 MHz, preferably 10 kHz to 1 MHz, and most preferably 400 kHz.

The electrosurgical instrument discussed herein may be capable of delivering radiofrequency (RF) electromagnetic (EM) energy and/or microwave EM energy into biological tissue. In particular, the electrosurgical instrument may be capable of delivering radiofrequency (RF) energy for cutting tissue and/or microwave frequency energy for haemostasis (i.e. sealing broken blood vessels by promoting blood coagulation). The invention may be particularly suitable in gastrointestinal (GI) procedures associated with the lower and upper GI tract, e.g. to remove polyps on the bowel, i.e. for endoscopic submucosal resection. The invention may also lend itself to precision endoscopic procedures, i.e. precision endoscopic resection, and may be used in ear, nose and throat procedures and liver resection. The device may also be used to address procedures associated with the pancreas, e.g. to resect or remove tumours or abnormalities in close proximity to the portal vein or the pancreatic duct.

BRIEF DESCRIPTION OF THE DRAWINGS

Examples embodying the invention are discussed in detail below with reference to the accompanying drawings, in which.

DETAILED DESCRIPTION; FURTHER OPTIONS AND PREFERENCES

Various aspects of the present inventions are presented below in the context of an electrosurgery system that provides an electrosurgical invasive instrument for use in endoscopic procedures for the removal of polyps and malignant growths through the controlled delivery of both microwave and RF energy. However, it is to be understood that the aspects of the invention presented herein need not be limited to this particular application. They may be equally applicable in embodiments where only RF energy is required, or where only RF energy and fluid delivery is required.

Figure 1:
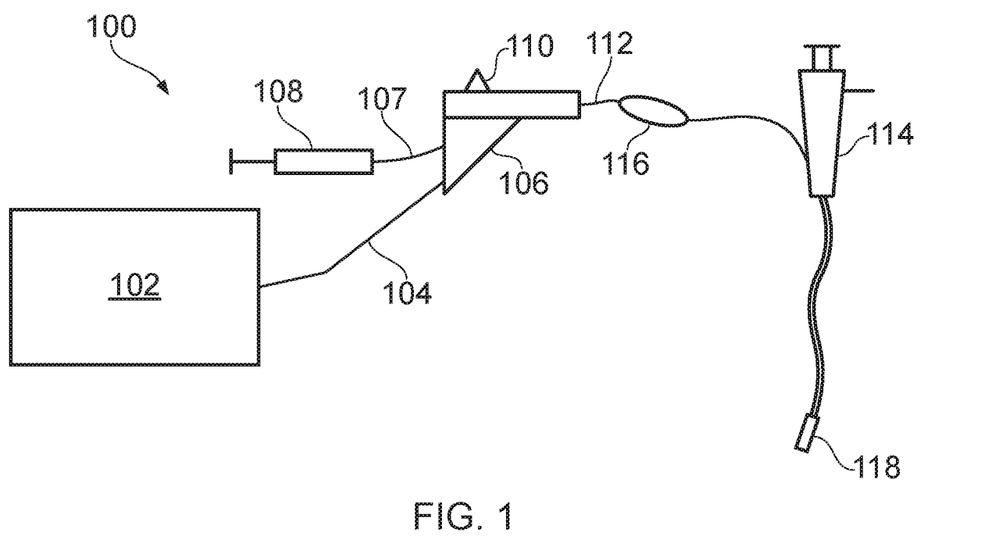
FIG. 1 is a schematic view of a complete electrosurgery system in which the present invention is applied.

FIG. 1 is a schematic diagram of a complete electrosurgery system 100 that is capable of selectively supplying to the distal end of an invasive electrosurgical instrument any or all of RF energy, microwave energy and fluid, e.g. saline or hyaluronic acid. The system 100 comprises a generator 102 for controllable supplying RF electromagnetic (EM) energy and/or microwave frequency EM energy. A suitable generator for this purpose is described in WO 2012/076844, which is incorporated herein by reference.

The generator 102 is connected to an interface joint 106 by an interface cable 104. The interface joint 106 is also connected to receive a fluid supply 107 from a fluid delivery device 108, such as a syringe. The interface joint 106 houses a needle movement mechanism that is operable by sliding a trigger 110. The function of the interface joint 106 is to combine the inputs from the generator 102, fluid delivery device 108 and needle movement mechanism into a single flexible shaft 112, which extends from the distal end of the interface joint 106. The internal configuration of the interface joint 106 is discussed in more detail below.

The flexible shaft 112 is insertable through the entire length of an instrument (working) channel of a surgical scoping device 114. A torque transfer unit 116 is mounted on a proximal length of the shaft 112 between the interface joint 106 and surgical scoping device 114. The torque transfer unit 116 engages the shaft to permit it to be rotated within the instrument channel of the surgical scoping device 114.

The flexible shaft 112 has an electrosurgical instrument tip 118 that is shaped to pass through the instrument channel of the surgical scoping device 114 and protrude (e.g. inside the patient) at the distal end of the endoscope's tube. The instrument tip includes an active tip for delivering RF EM energy and/or microwave EM energy into biological tissue and a retractable hypodermic needle for delivering fluid. These combined technologies provide a unique solution for cutting and destroying unwanted tissue and the ability to seal blood vessels around the targeted area. Through use of the retractable hypodermic needle, the surgeon is able to inject saline and/or hyaluronic acid with added marker dye between tissues layers in order to distend and mark the position of a lesion to be treated. The injection of fluid in this manner lifts and separates the tissue layers making it both easier to resect around the lesion and plane through the submucosal layer, reducing the risk of bowel wall perforation and unnecessary thermal damage to the muscle layer.

As discussed in more detail below, the instrument tip 118 further includes a protective hull positioned under the active tip to assist a tissue planing type resection action, again helping to protect against inadvertent perforation and ensure viability of the remaining tissue, which in turn facilitates more rapid healing and post operation recovery.

The structure of the instrument tip discussed below may be particularly designed for use with a conventional steerable flexible endoscope having a working channel with an internal diameters of at least 3.3 mm and a channel length of between 60 cm and 170 cm. As such the majority of the comparatively small diameter (less than 3 mm) instrument is housed within the lumen of a much larger and predominantly polymer insulating device, i.e. the flexible endoscope channel, which typically has an outer diameter of 11 mm to 13 mm. In practice, only 15 mm to 25 mm of the distal assembly protrudes from the distal end of the endoscope channel, in order not to block the field of view or adversely affect camera focusing. The protruding part of the distal assembly is the only portion of the instrument that ever makes direct contact with the patient.

At the proximal end of the endoscope working channel, which is typically held 50 cm to 80 cm from the patient, the flexible shaft 112 emerges from the working channel port and extends a further 30 cm to 100 cm to the interface joint 106. In use, the interface joint 106 is typically held by a gloved assistant throughout the procedure. The interface joint 106 is designed and manufactured from polymer materials in such a way as to provide primary and secondary electrical insulation with extended creepage and clearance distances. The interface cable 104 is connected to the generator 102 using a QMA-type coaxial interface, which is designed to allow continuous clockwise or counter clockwise rotation. This permits the interface joint 106 to rotate with the torque transfer unit 116 under the control of the user. The assistant supports the interface joint 106 throughout the procedure in order to assist the user with sympathetic instrument rotation, needle control and fluid injection.

Figure 2:
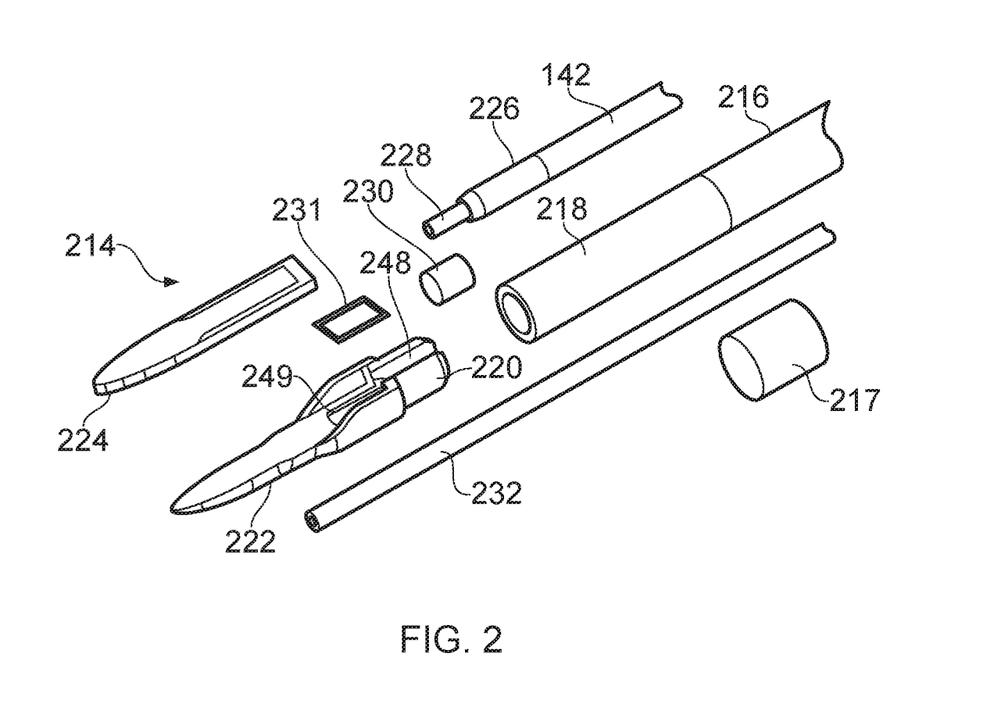
FIG. 2 is an exploded view of a distal end of an electrosurgical instrument that is an embodiment of the invention.

FIG. 2 shows an exploded view of the distal end assembly 214 (sometimes referred to as an instrument tip) of an electrosurgical instrument that is an embodiment of the invention. The distal end assembly 214 is mounted at the distal end of an outer cannula tube 216 of a flexible shaft, e.g. which correspond to the flexible shaft 112 discussed above with reference to FIG. 1. The cannula tube 216 forms a flexible sleeve defining a lumen for transporting fluid to the instrument tip, the instrument tip being secured at its distal end. In order to provide a torque transfer function, the outer cannula tube 216 is formed of a braided tube, e.g. comprising a braided wire (e.g. stainless steel) wrap mounted between a radially inner polymer layer and a radially outer polymer layer, wherein the polymer may be e.g. Pebax®.

In this embodiment, the outer cannula tube 216 is connected at its distal end to an unbraided tubular portion 218, which may be a flexible conduit. The tubular portion 218 may be formed from any suitable polymer material, e.g. Pebax® or the like. The tubular portion 218 may have an axial length (i.e. length in line with the shaft axis equal to or greater than 1 mm. This may ensure that a safe distance is introduced between the end of the braiding and the proximal edge of the distal end assembly 214 in order to avoid any risk of heating of the braid as a result of capacitive conductance during use of microwave energy. This arrangement may also prevent the two plates of the planar transmission line or the two conductors in the coaxial transmission line from becoming shorted or connected together.

The tubular portion 218 may be referred to as a 'soft tip' 218. The soft tip 218 may in some embodiments be an additional length of polymer tube which is bonded to the distal end of the sleeve or cannula tube 216. The bonding may use any suitable adhesive, e.g. epoxy or the like. A support tube 217 may be mounted over the junction between the tubular portion 218 and cannula tube 216 to reinforce the joint by providing additional mechanical strength. The support tube 217 may be a short section of polymer tubing within which the both the tubular portion 218 and the cannula tube 216 are secured, e.g. by bonding. The support tube 217 may be flexible and/or may have a length selected to ensure that it does not adversely affect the flexibility of the shaft.

The junction of the tubular portion 218, cannula tube 216 and support tube 217 may also be captured within a heat shrink sleeve (not shown) to provide further structural strength at the distal end of the shaft.

The braiding within the cannula tube 216 enables torque applied to the proximal end of the shaft to be transformed into rotational movement of the instrument tip. For convenience, some of the accompanying illustrations show the tubular portion 218 and cannula tube 216 as transparent. In practical embodiments, the shaft may be opaque.

A distal end of the tubular portion 218 is arranged to fit over a corresponding proximal part 220 of a protective hull 222. The protective hull is formed from a metallic material having low friction with biological tissue, e.g. stainless steel, and is shaped to perform a number of functions, i.e.

mount the distal end assembly 214 on the flexible shaft,
provide a protective undersurface for an active tip structure that delivers energy into surrounding biological tissue,
provide a protective housing and supporting frame for a retractable needle, and
locate the active tip structure relative to the coaxial cable during assembly and subsequent use.

The parts of the structure of the hull 222 that perform these functions are discussed in more detail below.

The distal end assembly 214 includes an active tip 224, which is a planar piece of dielectric material 221 (e.g. alumina) having conductive layers (e.g. layers of metallisation) on its upper and lower surfaces. The conductive layers are each electrically connected to a respective one of an inner conductor 228 and an outer conductor 226 of a coaxial cable 142 that is conveyed by the cannula tube 216. At a distal end of the coaxial cable 142, its outer sheath is removed to expose a length of the outer conductor 226. The inner conductor 228 of the coaxial cable extends beyond the distal end of the outer conductor 226. The coaxial cable 142 and the active tip 224 are mounted relative to one another so that the protruding part of the inner conductor 228 lies on a first conductive layer of the active tip, while the outer conductor 226 is brought into electrical connection with a second conductive layer via the protective hull 222, as discussed below. The first conductive layer is isolated from the outer conductor 226 and the second conductive layer is isolated from the inner conductor 228.

The conductive layers may be formed from high melting point conductors, e.g. W or Ti. However, in one example, to facilitate the use of solder in the electrical connection between the inner and outer conductors of the coaxial cable 142 and the active tip 224, lower melting point conductors may be deposited at proximal regions on the conductive layers where the electrical connections are made. The lower melting point conductors may be silver (Ag) or gold (Au).

The distal end of the active tip 224 is curved to avoid presenting sharp corners within the patient.

The outer conductor 226 is electrically connected to a lower conductive layer on the underside of the active tip 224 via the protective hull 222. A proximal end of the protective hull 222 is formed with a U-shaped channel 248 for receiving and supporting a distal end of the coaxial feed cable 142. The distal end assembly is configured so that the exposed portion of the outer conductor 226 sits in the U-shaped channel 248. An electrically conductive element 230, such as a sleeve or collar, is used to crimp the exposed portion of the outer conductor 226. The compression caused by the crimp means that the coaxial cable deforms in the region where it is received by the protective hull 222. For example, the portion of the coaxial cable where the outer conductor 226 is exposed may have an oval cross-section, whereby it abuts and forms a robust electrical contact with the sides of the U-shaped channel 248. The crimped outer conductor 226 may thus be retained by the hull via an interference fit.

Figure 5:
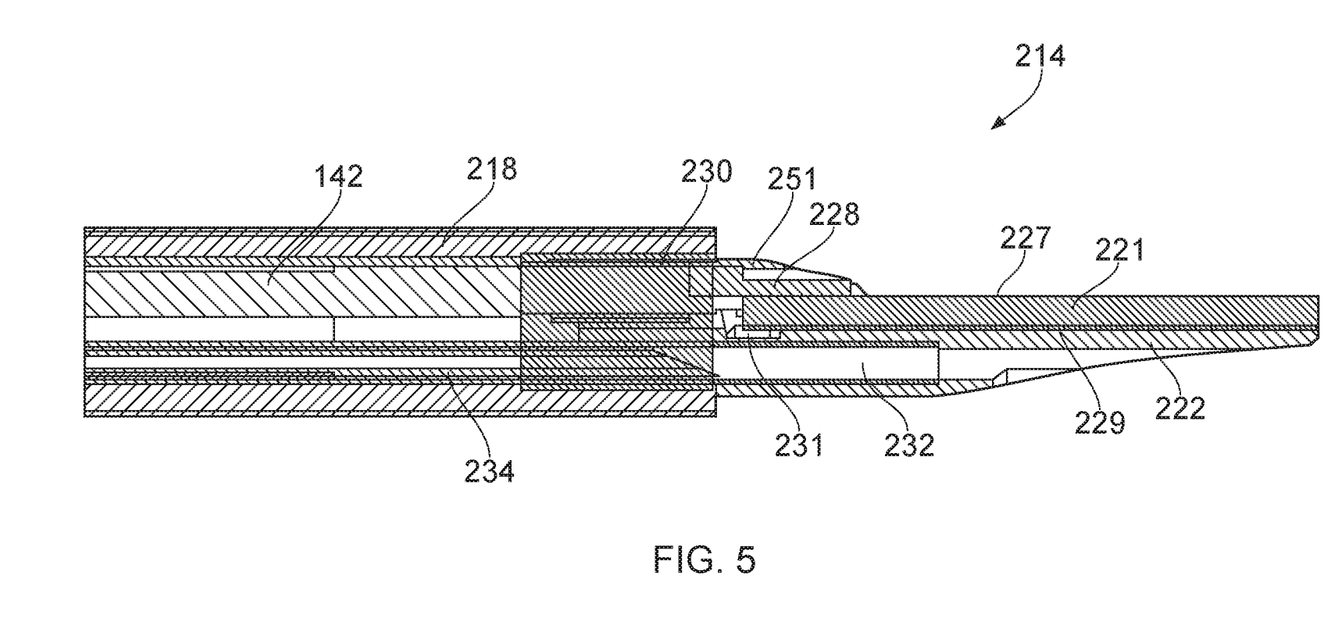
FIG. 5 is a cross-sectional side view of a distal tip assembly of an electrosurgical instrument that is an embodiment of the invention.

To complete the electrical connection between the outer conductor 226 and lower conductive layer 229 on the active tip 224, the protective hull 222 is electrically coupled to the lower conductive layer, e.g. by soldering (see e.g. FIG. 5). In this embodiment, a solder preform 231 is provided for this purpose. the solder preform 231 is shaped to be receivable within a recess 249 formed in an upper surface of the protective hull 222. In this example, the recess 49 is rectangular, and the solder preform 231 has a corresponding shape, but any suitable shape may be used. The recess 249 is set back from the edges of the protective hull in a manner that ensures solder is only present between the lower surface of the active tip 224 and the protective hull 222, i.e. it does not flow to the side edges of the active tip 224. When assembled, the solder preform 231 may be aligned with a region on the lower surface of the active tip 224 that is coated in a lower melting point conductor as discussed above (e.g. gold). A suitable flex (not shown) may be provided with the solder preform when the components are assembled to facilitate the soldering process. The soldering process itself may be induction soldering. The induction soldering effect may be confined to a region of the active tip 224 and protective hull 222 at the solder preform 231.

The above configuration is advantageous because the protective hull 222 retains all of (i) the active tip 224, (ii) the solder preform 231, and (iii) the coaxial cable 142 in a fixed spatial relationship which ensures accurate and repeatable assembly.

The distal end assembly further comprises a needle guide 232 that is retained within a recess formed in the undersurface of the protective hull 222. The needle guide 232 is a hollow tube (e.g. a ferrule), e.g. made of polyimide, within which a hypodermic needle 234 is slidably mounted. The needle 234 is in fluid communication with the internal volume of the cannula tube 216 in order to receive liquid present therein for delivery to the treatment site.

After the distal end assembly 214 is assembled, it may be secured within the distal end of the tubular portion 218 by an interference fit and an adhesive (e.g. epoxy). The adhesive may also form a plug for the distal end of the tubular portion 218 to provide a fluid tight seal that means the only exit for fluid introduced at the interface joint is through the needle 234. Similarly, the junction (e.g. soldered joint) between the inner conductor 228 and the upper conductive layer 227 may have a protective cover 251 (see FIG. 5) that may be formed from a suitable adhesive (e.g. epoxy). The protective cover 251 may strengthen the connection between the protective hull 222 and active tip 224, while also forming an end plug for the tubular portion 218, i.e. a fluid tight seal that means the only exit for fluid introduced at the interface joint is through the needle.

In use the active tip 224 makes an intimate contact with the patient. The needle 234 can be extended beyond the distal end of the active tip 224 and retracted to a position back inside the guide tube 232 via control of the slider mechanism on the interface joint which acts on a control wire 235 (see FIG. 3) to deploy and retract the needle 234. In its extended position, the needle is used to inject fluid for the purpose of locally distending and/or marking tissue. The conductive layers on the active tip 224 form bi-polar electrodes for delivering RF and/or microwave electromagnetic energy.

The needle guide 232 extends back inside and proximal to the distal assembly to provide extended creepage clearance to ensure RF/microwave activation only occurs across the distal tip region of the active tip 224.

Figure 3:
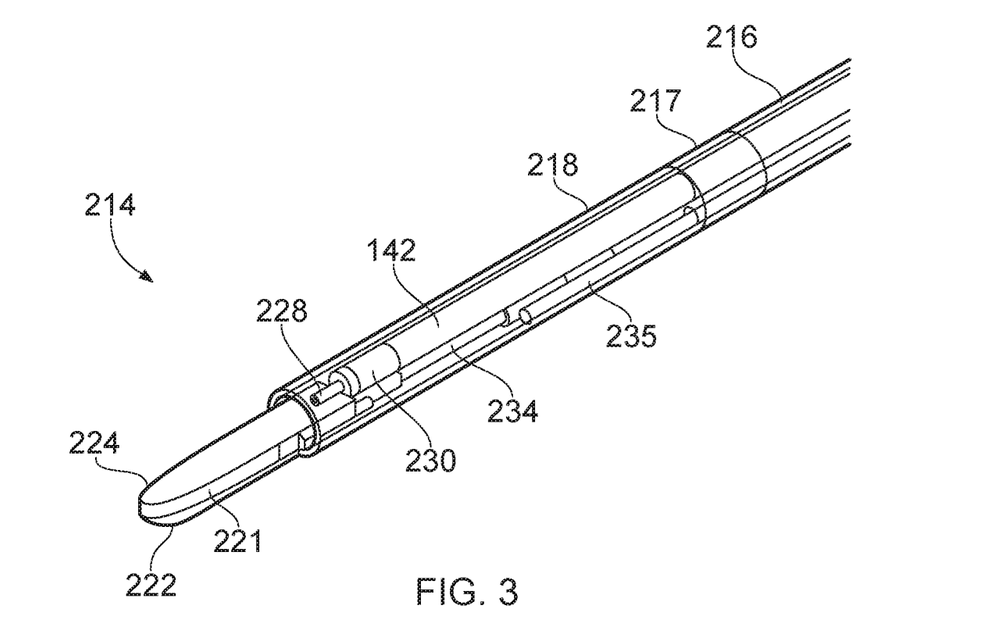
FIG. 3 is a partly transparent perspective view of a distal end of an electrosurgical instrument that is an embodiment of the invention.

FIG. 3 shows the distal end assembly 214 in an assembled configuration. The tubular portion 218, support sleeve 217 and cannula tube 216 are shown as transparent so that the inner components are visible. Parts of the protective hull 222 within the tubular portion 218 are omitted to show how the electrically conductive element 230 fits over the outer conductor 226.

Figure 4A:
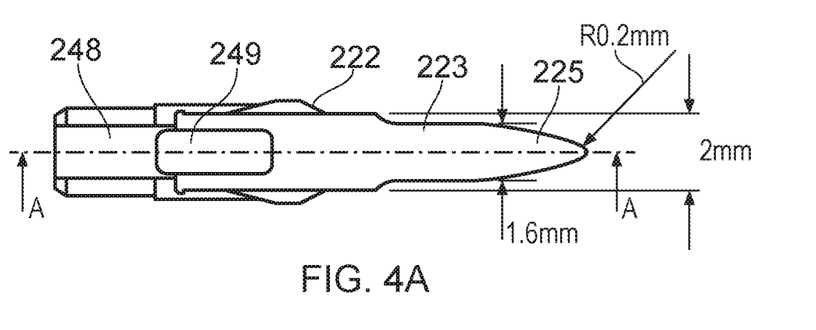
FIGS. 4A and 4B are a top view and a cross-sectional side view respectively of a protective hull member suitable for use with the present invention.
Figure 4B:
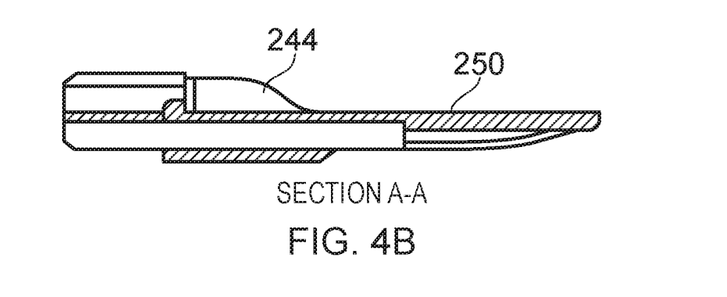

FIGS. 4A and 4B show the shape of a protective hull structure 222 that can be used in embodiments of the invention. A distal end of the protective hull 222 has a flat upper surface 250 for contacting the lower conductive layer 229 on the active tip 224. As discussed above, a rectangular recess 249 is formed towards the proximal end of the flat upper surface 250 for receiving the solder preform 231.

The proximal end of the protective hull 222 is formed with a U-shaped channel 248 for receiving and support the distal end of the coaxial feed cable 142. A similar channel is formed on the underside of the proximal end of the protective hull 222 to receive the guide tube 232 of the retractable needle 234. The outer surface of the proximal end of the protective hull 222 is cylindrical, with a diameter selected to fit inside the distal end of the tubular portion 218.

At the sides of the protective hull 222 between the proximal and distal ends, there are a pair of upstanding wing portions 244, whose inner surfaces engage with respective side edges of the active tip 224 and whose outer surface engage in an interference fit with the inner surface of the tubular portion 218.

The protective hull 222 is preferably made from a metallic material having a low coefficient of friction with biological tissue, such as stainless steel.

The distal end of the hull is shaped to permit the active tip 224 to overhang it by around 0.2 mm around the distal edge except at the distal tip. The surface that contacts the underside of the active tip therefore has a maximum width of 2 mm, which narrows to 1.6 mm in an intermediate portion 223 before tapering to its distal tip in a distal portion 225. The distal tip may be a single radiused curve, e.g. having a radius of 0.2 mm.

Meanwhile the proximal end of the hull defines an oblong recess for receiving the proximal end of the active tip. The oblong recess is bordered by a pair of wings 244 on each side, which act to retain and align the active tip as well as define a volume for receiving the protective cover 251 that covers the exposed inner conductor 228 of the coaxial cable 142.

FIG. 5 is a cross-section view through the distal end assembly 214 when fully assembled. Features described above are given the same reference number. In this drawings, the soldered conductive connection provided by the solder preform 231 is visible between the protective hull 222 and the lower conductive layer 229. To ensure secure bonding between the protective hull 222 and active tip 224, the lower conductive layer 229 may be bonded to the flat surface 250 where they abut distally from the soldered area.

The invention claimed is:

1. An electrosurgical instrument for delivering electromagnetic energy to biological tissue, the instrument comprising:
a distal end assembly comprising:
an active tip comprising a planar body made of a first dielectric material separating a first conductive element on a first surface thereof from a second conductive element on a second surface thereof, the second surface facing in the opposite direction to the first surface;
an electrically conductive protective hull mounted on an underside of the active tip, the protective hull having a smoothly contoured convex undersurface facing away from the planar body;
a coaxial feed cable comprising an inner conductor, an outer conductor coaxial with the inner conductor and a second dielectric material separating the inner and outer conductors, the coaxial feed cable being for conveying radiofrequency (RF) electromagnetic (EM) energy or microwave EM energy; and
an electrically conductive collar;
wherein the inner conductor is electrically connected to the first conductive element and the outer conductor is electrically connected to the second conductive element via the protective hull to enable the instrument tip to receive the RF and/or the microwave signal,
wherein the first and second conductive elements are arranged to emit the RF EM energy or the microwave EM energy from the coaxial feed cable at a distal side portion of the planar body,
wherein the protective hull is soldered to the second conductive element,
wherein the protective hull comprises an upper surface for abutting the second surface of the planar body, and wherein the upper surface comprises a recess for retaining a solder preform, and
wherein the protective hull has a U-shaped recess for receiving a portion of the coaxial feed cable comprising the inner conductor, the second dielectric material and the outer conductor, wherein the portion of the coaxial feed cable comprises an exposed portion of the outer conductor, wherein the exposed portion of the outer conductor is crimped by the electrically conductive collar, and wherein the portion of the coaxial feed cable is crimped to cause the portion of the coaxial feed cable to deform within the U-shaped recess to retain the coaxial feed cable in the U-shaped recess by an interference fit.

2. The electrosurgical instrument according to claim 1, wherein the protective hull comprises a piece of stainless steel.

3. The electrosurgical instrument according to claim 1, wherein the recess has side edges that are set back from side edges of the planar body.

4. The electrosurgical instrument according to claim 1, wherein the distal end assembly comprises a flexible shaft connected to a proximal end of the protective hull, the shaft defining a lumen for conveying the coaxial feed cable.

5. The electrosurgical instrument according to claim 4, wherein the flexible shaft comprises:
   a proximal cannula tube having braids formed therein to assist in a transfer of torque from its proximal end to the distal end assembly; and
   a distal unbraided tubular portion bonded to a distal end of the cannula tube.

6. The electrosurgical instrument according to claim 5, wherein the flexible shaft comprises a support tube mounted at a junction between the proximal cannula tube and the unbraided tubular portion.

7. The electrosurgical instrument according to claim 5, wherein a junction between the proximal cannula tube and the unbraided tubular portion is wrapped in a heat shrink sleeve.

8. The electrosurgical instrument according to claim 1, wherein the first and second conductive elements each comprise a layer of metallisation, the layers of metallisation being formed on opposite surfaces of the first dielectric material.

9. The electrosurgical instrument according to claim 8, wherein each layer of metallisation comprises a plated region formed from a metal having a melting point higher than 1500° C.

10. The electrosurgical instrument according to claim 9, wherein the first conductive element comprises a first connecting portion between its plated region and the inner conductor and the second conductive element comprises a second connecting portion between its plated region and the protective hull, wherein the first and second connecting portions are made from a conductive material having a melting point less than 1200° ° C.

11. The electrosurgical instrument according to claim 9, wherein the metal having a melting point higher than 1500° C. is titanium or tungsten.

12. The electrosurgical instrument according to claim 1, wherein the distal end assembly includes a fluid feed conduit for conveying fluid for delivery out of the instrument.

13. The electrosurgical instrument according to claim 12, wherein the undersurface of the protective hull has a longitudinally extending recessed channel formed therein, and wherein the fluid feed conduit is mounted within the longitudinally extending recessed channel.

14. The electrosurgical instrument according to claim 12, wherein the fluid feed conduit comprises a needle guide tube having a retractable needle slidably mounted therein.

* * * * *